(12) United States Patent
Chiu et al.

(10) Patent No.: US 9,221,873 B1
(45) Date of Patent: Dec. 29, 2015

(54) SHORT-CHAIN PEPTIDE CAPABLE OF CONTROLLING SPERMATOZOA FERTILIZATION PERFORMANCE

(71) Applicant: NATIONAL TAIWAN UNIVERSITY, Taipei (TW)

(72) Inventors: Chih-Hsien Chiu, Taipei (TW); Meng-Chieh Hsu, Taipei (TW)

(73) Assignee: NATIONAL TAIWAN UNIVERSITY (TW)

( * ) Notice: Subject to any disclaimer, the term of this patent is extended or adjusted under 35 U.S.C. 154(b) by 0 days.

(21) Appl. No.: 14/494,622

(22) Filed: Sep. 24, 2014

(30) Foreign Application Priority Data

Aug. 12, 2014 (TW) ................................ 103127557 A

(51) Int. Cl.
*A61K 38/00* (2006.01)
*C07K 5/00* (2006.01)
*C07K 7/00* (2006.01)
*C07K 16/00* (2006.01)
*C07K 17/00* (2006.01)
*C07K 7/06* (2006.01)
*C07K 14/47* (2006.01)

(52) U.S. Cl.
CPC . *C07K 7/06* (2013.01); *C07K 14/47* (2013.01); *C07K 14/4705* (2013.01)

(58) Field of Classification Search
None
See application file for complete search history.

(56) References Cited

U.S. PATENT DOCUMENTS 7,754,220 B2 *  7/2010  Ohtaki et al. ............... 424/198.1

FOREIGN PATENT DOCUMENTS

WO    WO2005117939    *  4/2005  ............. A61K 38/17

OTHER PUBLICATIONS

Hsu et al. Kisspeptin modulates fertilization capacity of mouse spermatozoa. Reproduction, Feb. 2014, pp. 835-845.*

* cited by examiner

Primary Examiner — Marcela M Cordero Garcia
(74) Attorney, Agent, or Firm — Schmeiser, Olsen & Watts, LLP

(57) ABSTRACT

A short-chain peptide capable of controlling spermatozoa fertilization performance is supplied in an in vitro culture medium of spermatozoa and oocytes to increase the success rates of in vitro fertilization. The short-chain peptide comprises an amino acid sequence H-Tyr-Asn-Trp-Asn-Ser-Phe-Gly-Leu-Arg-X-NH2 (SEQ ID NO: 1), where X denotes Tyr or Phe, and the sequence ends with an amide. The short-chain peptide is conducive to adjustment of the concentration of free calcium ions inside the cells of the spermatozoa and thus enhancement of the success rates of in vitro fertilization.

7 Claims, 2 Drawing Sheets

SEQUENCE LISTING

```
<160> NUMBER OF SEQ ID NOS: 11

<210> SEQ ID NO 1
<211> LENGTH: 10
<212> TYPE: PRT
<213> ORGANISM: Artificial Sequence
<220> FEATURE:
<223> OTHER INFORMATION: short-chain peptide is supplied in an in vitro
      culture medium of spermatozoa and oocytes with a view to
      increasing the success rates of in vitro fertilization
<220> FEATURE:
<221> NAME/KEY: binding
<222> LOCATION: (1)..(1)
<223> OTHER INFORMATION: Hydrogen
<220> FEATURE:
<221> NAME/KEY: MISC_FEATURE
<222> LOCATION: (10)..(10)
<223> OTHER INFORMATION: Tyrosine or Phenylalanine
<220> FEATURE:
<221> NAME/KEY: BINDING
<222> LOCATION: (10)..(10)
<223> OTHER INFORMATION: NH2

<400> SEQUENCE: 1

Tyr Asn Trp Asn Ser Phe Gly Leu Arg Xaa
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Human expressed kisspeptin-10
<220> FEATURE:
<221> NAME/KEY: BINDING
<222> LOCATION: (10)..(10)
<223> OTHER INFORMATION: NH2

<400> SEQUENCE: 2

Tyr Asn Trp Asn Ser Phe Gly Leu Arg Phe
1               5                   10
```

-continued

```
<210> SEQ ID NO 3
<211> LENGTH: 13
<212> TYPE: PRT
<213> ORGANISM: Artificial Sequence
<220> FEATURE:
<223> OTHER INFORMATION: Human expressed kisspeptin-13
<220> FEATURE:
<221> NAME/KEY: Binding
<222> LOCATION: (13)..(13)
<223> OTHER INFORMATION: NH2

<400> SEQUENCE: 3

Leu Pro Asn Tyr Asn Trp Asn Ser Phe Gly Leu Arg Phe
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Human expressed kisspeptin-14
<220> FEATURE:
<221> NAME/KEY: binding
<222> LOCATION: (14)..(14)
<223> OTHER INFORMATION: NH2

<400> SEQUENCE: 4

Asp Leu Pro Asn Tyr Asn Trp Asn Ser Phe Gly Leu Arg Phe
1               5                   10

<210> SEQ ID NO 5
<211> LENGTH: 54
<212> TYPE: PRT
<213> ORGANISM: Artificial Sequence
<220> FEATURE:
<223> OTHER INFORMATION: human express kisspeptin-54
<220> FEATURE:
<221> NAME/KEY: binding
<222> LOCATION: (54)..(54)
<223> OTHER INFORMATION: NH2

<400> SEQUENCE: 5

Gly Thr Ser Leu Ser Pro Pro Pro Glu Ser Ser Gly Ser Pro Gln Gln
1               5                   10                  15

Pro Gly Leu Ser Ala Pro His Ser Arg Gln Ile Pro Ala Pro Gln Gly
            20                  25                  30

Ala Val Leu Val Gln Arg Glu Lys Asp Leu Pro Asn Tyr Asn Trp Asn
        35                  40                  45

Ser Phe Gly Leu Arg Phe
    50

<210> SEQ ID NO 6
<211> LENGTH: 10
<212> TYPE: PRT
<213> ORGANISM: Artificial Sequence
<220> FEATURE:
<223> OTHER INFORMATION: Rodent expressed kisspeptin-10
<220> FEATURE:
<221> NAME/KEY: Binding
<222> LOCATION: (10)..(10)
<223> OTHER INFORMATION: NH2

<400> SEQUENCE: 6

Tyr Asn Trp Asn Ser Phe Gly Leu Arg Tyr
1               5                   10
```

```
<210> SEQ ID NO 7
<211> LENGTH: 13
<212> TYPE: PRT
<213> ORGANISM: Artificial Sequence
<220> FEATURE:
<223> OTHER INFORMATION: Rodent expressed kisspeptin-13
<220> FEATURE:
<221> NAME/KEY: binding
<222> LOCATION: (13)..(13)
<223> OTHER INFORMATION: NH2

<400> SEQUENCE: 7

Leu Ser Thr Tyr Asn Trp Asn Ser Phe Gly Leu Arg Tyr
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Rodent expressed kisspeptin-14
<220> FEATURE:
<221> NAME/KEY: binding
<222> LOCATION: (14)..(14)
<223> OTHER INFORMATION: NH2

<400> SEQUENCE: 8

Asp Leu Ser Thr Tyr Asn Trp Asn Ser Phe Gly Leu Arg Tyr
1               5                   10

<210> SEQ ID NO 9
<211> LENGTH: 52
<212> TYPE: PRT
<213> ORGANISM: Artificial Sequence
<220> FEATURE:
<223> OTHER INFORMATION: Rodent expressed kisspeptin--52
<220> FEATURE:
<221> NAME/KEY: binding
<222> LOCATION: (52)..(52)
<223> OTHER INFORMATION: NH2

<400> SEQUENCE: 9

Ser Ser Pro Cys Pro Pro Val Glu Gly Pro Ala Gly Arg Gln Arg Pro
1               5                   10                  15

Leu Cys Ala Ser Arg Ser Arg Leu Ile Pro Ala Pro Arg Gly Ala Val
                20                  25                  30

Leu Val Gln Arg Glu Lys Asp Leu Ser Thr Tyr Asn Trp Asn Ser Phe
        35                  40                  45

Gly Leu Arg Tyr
    50

<210> SEQ ID NO 10
<211> LENGTH: 10
<212> TYPE: PRT
<213> ORGANISM: Artificial Sequence
<220> FEATURE:
<223> OTHER INFORMATION: Kisspeptin antagonist peptide 234
<220> FEATURE:
<221> NAME/KEY: MOD_RES
<222> LOCATION: (1)..(1)
<223> OTHER INFORMATION: ACETYLATION
<220> FEATURE:
<221> NAME/KEY: SITE
<222> LOCATION: (1)..(1)
<223> OTHER INFORMATION: D-Alanine
<220> FEATURE:
<221> NAME/KEY: SITE
<222> LOCATION: (8)..(8)
<223> OTHER INFORMATION: D-tryptophan
```

```
<220> FEATURE:
<221> NAME/KEY: BINDING
<222> LOCATION: (10)..(10)
<223> OTHER INFORMATION: NH2

<400> SEQUENCE: 10

Ala Asn Trp Asn Gly Phe Gly Trp Arg Phe
1               5                   10

<210> SEQ ID NO 11
<211> LENGTH: 10
<212> TYPE: PRT
<213> ORGANISM: Artificial Sequence
<220> FEATURE:
<223> OTHER INFORMATION: short-chain peptide capable of controlling
      spermatozoa fertilization performance
<220> FEATURE:
<221> NAME/KEY: MISC_FEATURE
<222> LOCATION: (10)..(10)
<223> OTHER INFORMATION: Tyrosine or Phenylalanine
<220> FEATURE:
<221> NAME/KEY: binding
<222> LOCATION: (10)..(10)
<223> OTHER INFORMATION: NH2

<400> SEQUENCE: 11

Tyr Asn Trp Asn Ser Phe Gly Leu Arg Xaa
1               5                   10
```

SHORT-CHAIN PEPTIDE CAPABLE OF CONTROLLING SPERMATOZOA FERTILIZATION PERFORMANCE

CROSS-REFERENCE TO RELATED APPLICATION

This non-provisional application claims priority under 35 U.S.C. §119(a) on Patent Application No(s).103127557 filed in Taiwan, R.O.C. on Aug. 12, 2014, the entire contents of which are hereby incorporated by reference.

SEQUENCE LISTING

A Sequence Listing required by 37 C.F.R. §1.821(c) has been submitted along with this application in a Computer Readable form in accordance with 37 C.F.R. 1.824. As required 37 C.F.R. §1.52(e)(5), the Sequence Listing accompanying this application is hereby incorporated-by-reference.

FIELD OF THE INVENTION

The present invention relates to short-chain peptides capable of controlling spermatozoa fertilization capability, and more particularly, to a short-chain peptide supplied in an in vitro culture medium of spermatozoa and oocytes to increase the success rates of in vitro fertilization.

BACKGROUND OF THE INVENTION

Fertilization begins with the fusion of a sperm and an oocyte. Experiments conducted by scientists verified that fertilization does not happen simply as a result of insemination following ovulation, but several hours before ovulation. The aforesaid phenomenon is described by capacitation which refers to the physiological changes spermatozoa must undergo in order to have the ability to penetrate and fertilize an oocyte. The time taken to effectuate the physiological changes varies with species, namely 5 hours among rabbits, 1 hour among mice, 2~3 hours among rats, and 5~6 hours among human beings.

Although its discovery dates back to 1951, capacitation is not well understood in terms of molecular regulatory mechanism and signal transduction pathways. The capacitation-induced physiological changes in spermatozoa include increased membrane fluidity, cholesterol efflux, changes in the intracellular concentration of ions, hyperpolarization, alkalization, tyrosine phosphorylation, and hyperactivation. Up to now, controlling capacitation includes at least three pathways: cAMP/PKA-dependent pathway, receptor tyrosine kinase-dependent pathway, and non-receptor tyrosine kinase-dependent pathway. All the three pathways bring about tyrosine phosphorylation, thereby capacitating spermatozoa.

Known factors in capacitation include cholesterol, calcium ions, bicarbonate ions, ROS (reactive oxygen species), progesterone, GABA (gamma-aminobutyric acid), and decapacitation factor. Among the aforesaid factors, calcium ion is a critical regulator.

Calcium influx plays an important role in both capacitation and the subsequent acrosome reaction. Research finds a marked increase in the intracellular concentration of calcium ions in mammalian spermatozoa during capacitation. To effectuate capacitation, the extracellular concentration of calcium ions in spermatozoa varies with species, namely micromolar among mouse spermatozoa, and millimolar among human spermatozoa.

Research also finds that calcium ion concentration of 0.22 mM is required for capacitation of human spermatozoa, and that calcium ion concentration of at least 0.58 mM is required for the subsequent acrosome reaction and the binding of spermatozoa to the zona pellucida, indicating that at the moment when calcium influx takes place the required calcium ion concentration varies from stage to stage. Prior to capacitation, the intracellular concentration of calcium ions in spermatozoa is maintained at lower level by the intracellular calcium ion exchange systems in spermatozoa, such as voltage-dependent calcium channel, and $Ca^{2+}$/ATPase, and $Na^+$-$Ca^{2+}$exchanger. The success rates of in vitro fertilization can be increased by introducing calcium ions into spermatozoa or triggering calcium ion-storing organelles of the spermatozoa to release calcium ions into sperm cytoplasm, so as to increase the intracellular calcium ion concentration during capacitation to thereby enhance intracellular signal delivery, promote the subsequent hyperactivation, and induce the subsequent acrosome reaction.

Ligand kisspeptins, which are discovered in human placenta and found to demonstrate high affinity to GPR54, is translated from KISS1 gene. The precursory product of KISS1 gene is a protein that contains 145 amino acids, and then the protein is hydrolyzed by protease to produce a peptide composed of 54 amino acids and known as kisspeptin-54. From the very beginning, kisspeptin-54 is called metastin, because its genes are believed to be capable of inhibiting the metastasis of melanomas.

In addition to kisspeptin-54, small-sized segment peptides derived from kisspeptin precursors are identified, including kisspeptin-14, kisspeptin-13, and kisspeptin-10. Identical structures known as RF-amide motif (Arg-Phe-NH2) are disposed at the C-terminal of the peptides. All the different length peptides can bind to GPR54 and manifest the same degree of affinity thereto.

In vitro fertilization involves taking oocytes and spermatozoa out of a female human body and a male human body, respectively, rinsing the oocytes and spermatozoa, culturing oocytes and spermatozoa together until the fusion of an oocyte and a spermatozoa occurs to begin the fertilization process, culturing the fertilized oocyte for 3~6 days before putting it back to the female human body. Three to six instances of artificial insemination failure, severe endometriosis, and would-be mothers of advanced age are indications for in vitro fertilization.

The success rates of conventional in vitro fertilization are unsatisfactorily low, i.e., 30~40%. The success rates of in vitro fertilization among mice varies with strains and stands at 10~90%. Accordingly, it is imperative to improve in vitro fertilization and increase its success rates.

SUMMARY OF THE INVENTION

In view of the aforesaid drawbacks of the prior art, it is an objective of the present invention to provide a short-chain peptide supplied in an in vitro culture medium of spermatozoa and oocytes to increase the success rates of in vitro fertilization.

In order to achieve the above and other objectives, the present invention provides a short-chain peptide conducive to the control of spermatozoa fertilization performance. The short-chain peptide is supplied in an in vitro culture medium of spermatozoa and oocytes with a view to increasing the success rates of in vitro fertilization. The short-chain peptide includes an amino acid sequence H-Tyr-Asn-Trp-Asn-Ser-Phe-Gly-Leu-Arg-X-NH2 (SEQ ID NO: 1), wherein X denotes Tyr or Phe, and the sequence ends with an amide.

The short-chain peptide is of a concentration higher than 25 μM, preferably 50 μM~100 1.1M, much preferably 50 μM, and most preferably 100 μM.

The short-chain peptides imply human expressed kisspeptins, including kisspeptin-54 (SEQ ID NO:5), kisspeptin-14 (SEQ ID NO:4), kisspeptin-13 (SEQ ID NO:3), and kisspeptin-10 (SEQ ID NO:2).

The short-chain peptides imply rodent expressed kisspeptins, including kisspeptin-52 (SEQ ID NO:9), kisspeptin-14 (SEQ ID NO:8), kisspeptin-13 (SEQ ID NO:7), and kisspeptin-10 (SEQ ID NO:6).

The short-chain peptide of the present invention, supplied in an in vitro fertilization culture medium, serves to increase the intracellular concentration of free calcium ions in spermatozoa, effectuate capacitation during a fertilization process, and thus increase the success rates of in vitro fertilization.

BRIEF DESCRIPTION OF THE DRAWINGS

Objectives, features, and advantages of the present invention are hereunder illustrated with specific embodiments in conjunction with the accompanying drawings, in which.

DETAILED DESCRIPTION OF THE PREFERRED EMBODIMENTS

I. Animal and Material

Figure 1:
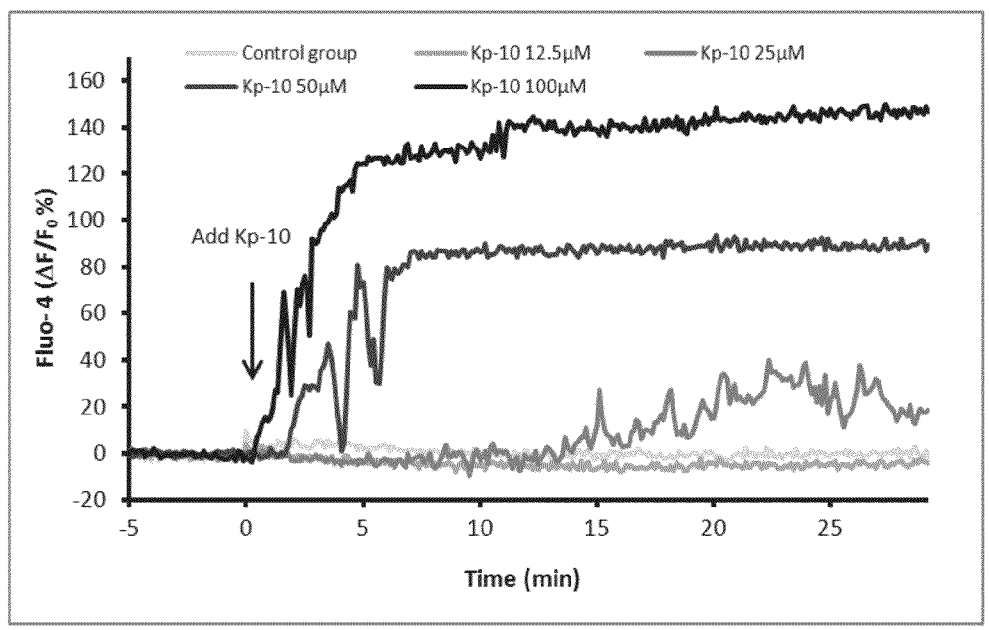
FIG. 1 is a graph of changes in the intracellular concentration of free calcium ions in spermatozoa against time, wherein different concentration short-chain peptides are supplied in sperm culture medium.

Animal subjects, namely ICR (imprinting control region) mice, male adults (10-16 weeks old) and female adults (8-12 weeks old), are purchased from the Experimental Animal Center, Medical College, National Taiwan University. The mice are kept in an environment characterized in that 12 hours of brightness (08:00-20:00) alternates with 12 hours of darkness (20:00-08:00) at a room temperature of 21±2° C., and provided chow diet and water ad libitum during the study.

The short-chain peptide kisspeptin-10 (SEQ ID NO:6) and antagonist peptide-234 (SEQ ID NO:10) used in the experiments are purchased from Kelowna international Scientific (Taipei, Taiwan), and the other related reagents are purchased from sigma Aldrich and Invitrogen.

II. Separating Spermatozoa

Spermatozoa are prepared for measuring changes in the intracellular concentration of free calcium ions ($[Ca^{2+}]_i$). Modified HEPES medium (120 mM of NaCl, 2 mM of KCl, 1.2 mM of $MgSO_4 \cdot 7H_2O$, 0.36 mM of $NaH_2PO_4$, 15 mM of $NaHCO_3$, 10 mM of HEPES, 5.6 mM of glucose, 1.1 mM of sodium pyruvate, 18.5 mM of sucrose, 100 IU/ml of penicillin, and 100 μg/ml of streptomycin), spermatozoa culture medium, is pre-incubated in incubator with 5% $CO_2$ at 37° C. for 24 hours before using to adjust the medium pH ranges between 7.3 and 7.4. The cauda epididymis is cut into several pieces, incubated in the medium at 37° C. for 20 minutes, put on 1 ml of 75% (v/v) Percoll solution, and centrifuged at 300×g for 30 minutes to isolate higher motility spermatozoa for $[Ca^{2+}]_i$ measurement experiment.

In the in vitro fertilization experiment, spermatozoa isolated from cauda epididymis are incubated in HTF (human tubal fluid) medium (Merck Millipore) at 37° C. for 20 minutes and then diluted the cell concentration to $1 \times 10^6$ spermatozoa per milliliter.

III. Measuring the $[Ca^{2+}]_i$ in Spermatozoa.

Changes in the $[Ca^{2+}]_i$ in uncapacitated spermatozoa are measured. Spermatozoa ($1 \times 10^8$ cells per milliliter) is incubated in modified HEPES medium, containing 15 μM of Fluo-4 AM, in the darkness at 37° C. for 45 minutes. Fluo-4 AM is a fluorescent $Ca^{2+}$ indicator capable of penetrating cell membranes. Then, the spermatozoa are washed thrice by 100×g centrifugation at room temperature for 5 minutes to remove the residual dye. The sperm cell pellet is suspended in a modified HEPES medium, containing 1.8 mM of $CaCl_2$, and the cell concentration is adjusted to $5 \times 10^6$ cells per milliliter. Then, the spermatozoa are loaded into a 96-well assay black plate, wherein each well is filled with 100 μl of sperm suspension. The changes of fluorescent intensity are measured with the Synergy H1 Hybrid Multi-Mode Microplate Reader (Bio-Tek, Winooski, Vt., USA) at 37° C. via an excitation wavelength of 485 nm and an emission wavelength of 520 nm. Afterward, 100 μl kisspeptin-10 solution (1:1 diluted) in different concentrations (0-100 μM) is added to the sperm suspension, to test the effects of kisspeptin-10 on the changes in $[Ca^{2+}]_i$ in spermatozoa. Changes in $[Ca^{2+}]_i$ are calculated with the equation $(F'-F_0)/F_0$ (%), wherein F' denotes the fluorescent intensity measured at different time points during the experiment, and $F_0$ denotes the average of fluorescent intensity measured 0 to 5 minutes before adding kisspeptin-10. Last but not least, the average change in the fluorescent intensity during the plateau phase (27~30 minutes) of $[Ca^{2+}]_i$ is calculated.

IV. IVF Test

The uncapacitated spermatozoa is incubated in HTF medium and then treated with peptide 234 during capacitation step, such that kisspeptin signal effects on final fertilization step is evaluated. The 0.9% saline is added to the control group to substitute for the peptide 234 solution. In detail, spermatozoa ($1 \times 10^6$ cell per milliliter) are incubated in a capacitation-condition medium with 50 μM peptide 234 or saline at 37° C. for 2 hours. Then, the fertilization process begins with the introduction of cumulus-oocyte complexes (COCs) into the culture medium and incubation at 37° C. for 6 hours. The oocytes are washed thrice and incubated in KSOM+AAs culture medium (potassium simplex optimized medium plus amino acids, Merk Millipore) for 24 hours. The success fertilization rate is calculated according to the ratio of the number of two-cell embryos to the total number of oocytes.

The COCs are prepared as follows: intraperitoneal injection of 10 IU of pregnant mare serum gonadotrophin (PMSG) and 10 IU of human chorionic gonadotropin (hCG), both of which are purchased from China Chemical & Pharmaceutical Co., Ltd. (Taipei, Taiwan), into female mice at a time interval of 48 hours; and, 12-14 hours after the injection of hCG, the COCs is taken from the ampulla and cultured in HTF medium.

Results

Effects of Kisspeptins on $[Ca^{2+}]_i$ in Spermatozoa

The experiment finds that kisspeptins play an important role in the regulation of sperm functions, because kisspeptins correlate with changes in $[Ca^{2+}]_i$. Referring to FIG. 1, $[Ca^{2+}]*_i$ increases when mouse spermatozoa are treated with 25, 50 and 100 μM of kisspeptin 10, based on the fluorescent intensity increases markedly. As shown in FIG. 1, mouse spermatozoa are treated with 50 and 100 μM of kisspeptin 10, $[Ca^{2+}]_i$ increases by 85.5±14.4% and 129.9±24.9%, respectively. Hence, if the kisspeptin 10 concentration is higher in the culture medium, the intracellular concentration of free calcium ions in the spermatozoa will increase. With free calcium ion concentration increasing, the chance of the capacitation of the spermatozoa augments; hence, the introduction of short-chain peptides into an in vitro culture medium increases the success rates of in vitro fertilization.

Although the aforesaid experiment requires kisspeptin 10, persons skilled in the art understand that any short-chain peptides as active as kisspeptin 10 bring about the same result. Hence, if human expressed kisspeptins, including kisspeptin-54, kisspeptin-14, kisspeptin-13 and kisspeptin-10, or rodent expressed kisspetins, including kisspeptin-52, kisspeptin-14, kisspeptin-13 and kisspeptin-10, are added to an in vitro culture medium, the spermatozoa $[Ca^{2+}]_i$ will increase, thereby increasing the success rates of in vitro fertilization.

Effects of Kisspeptin Antagonist on Spermatozoa Fertilization Performance

Figure 2:
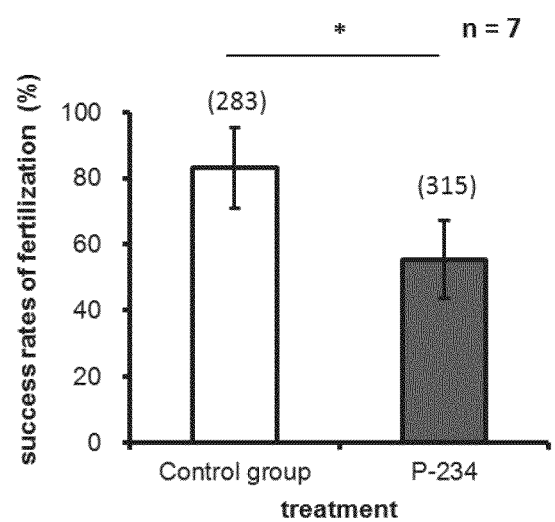
FIG. 2 is a bar diagram of the success rates of in vitro fertilization as a result of supplement with kisspeptin antagonist peptide 234 (SEQ ID NO:10) in a culture medium and a control group for use in in vitro fertilization, respectively.

Adding kisspeptin antagonist peptide 234 to a culture medium for use in in vitro fertilization brings about the result illustrated with FIG. 2. Referring to FIG. 2, the success fertilization rates among the control group are larger than 80%, whereas the culture medium treated with kisspeptin antagonist peptide 234 reduces the success fertilization rates to less than 60%, because kisspeptin antagonist peptide 234 binds to KISS1R on the spermatozoa to block the functional pathway of kisspeptin, thereby proving that kisspeptins are capable of increasing the success rates of in vitro fertilization.

In conclusion, the aforesaid experiment shows that: adding kisspeptin to a culture medium for use in in vitro fertilization effectively increases the spermatozoa $[Ca^{2+}]_i$ and thus promotes the capacitation of the spermatozoa; and adding kisspeptin antagonist peptide 234 to a culture medium for use in in vitro fertilization decreases the success rates of in vitro fertilization. Hence, the aforesaid experiment proves that the kisspeptin plays an indispensable role in in vitro fertilization as the presence of the kisspeptin in a culture medium for use in in vitro fertilization increases the success rates of in vitro fertilization.

The present invention is disclosed above by preferred embodiments. However, persons skilled in the art should understand that the preferred embodiments are illustrative of the present invention only, but should not be interpreted as restrictive of the scope of the present invention. Hence, all equivalent modifications and replacements made to the aforesaid embodiments should fall within the scope of the present invention. Accordingly, the legal protection for the present invention should be defined by the appended claims.

What is claimed is:

1. A method of using a peptide to control spermatozoa fertilization performance and increase success rates of in vitro fertilization comprising, supplying the peptide in an in vitro culture medium of spermatozoa and oocytes wherein:
the peptide includes an amino acid sequence (SEQ ID NO:1) H-Tyr-Asn-Trp-Asn-Ser-Phe-Gly-Leu-Arg-X-NH$_2$, wherein X denotes one of Tyr and Phe, and the sequence ends with an amide.

2. The method of claim 1, wherein the peptide is of a concentration higher than 25 μM.

3. The method of claim 2, wherein the peptide is of a concentration of 50 μM~100 μM.

4. The method of claim 2, wherein the peptide is of a concentration of 50 μM.

5. The method of claim 2, wherein the peptide is of a concentration of 100 μM.

6. The method chain peptide of claim 1, wherein the peptide includes a human phenotype peptide of kisspeptin-54 (SEQ ID NO:5), kisspeptin-14 (SEQ ID NO:4), kisspeptin-13 (SEQ ID NO:3), and kisspeptin-10 (SEQ ID NO:2).

7. The method of claim 1, wherein the peptide includes rodent expressed kisspeptins, including kisspeptin-52 (SEQ ID NO:9), kisspeptin-14 (SEQ ID NO:8), kisspeptin-13 (SEQ ID NO:7), and kisspeptin-10 (SEQ ID NO:6).

* * * * *